United States Patent [19]

Linton

[11] 4,088,473

[45] May 9, 1978

[54] HERBICIDAL COMPOSITION FOR WEED CONTROL

[76] Inventor: Thomas Harry Linton, 48 Farmcrest Dr., Agincourt, Ontario, Canada

[21] Appl. No.: 789,048

[22] Filed: Apr. 20, 1977

Related U.S. Application Data

[60] Continuation-in-part of Ser. No. 548,947, Feb. 11, 1975, abandoned, which is a division of Ser. No. 440,940, Feb. 8, 1974, Pat. No. 3,925,927.

[30] Foreign Application Priority Data

Feb. 7, 1974  Canada ................................ 191984

[51] Int. Cl.$^2$ .......................... A01N 9/22; A01N 9/24
[52] U.S. Cl. ............................................ 71/92; 71/3; 71/11; 71/64 F; 71/79; 71/113; 71/114; 71/116; 71/117; 71/DIG. 1
[58] Field of Search ..................... 71/79, DIG. 1, 116, 71/117, 114, 92, 113

[56] References Cited

U.S. PATENT DOCUMENTS

| | | | |
|---|---|---|---|
| 2,992,090 | 7/1961 | Littler | 71/DIG. 1 |
| 3,130,124 | 4/1964 | Ferris et al. | 71/DIG. 1 |
| 3,725,031 | 4/1973 | Balassa | 71/79 X |

FOREIGN PATENT DOCUMENTS

| | | | |
|---|---|---|---|
| 612,956 | 1/1961 | Canada | 71/DIG. 1 |
| 893,818 | 4/1962 | United Kingdom | 71/DIG. 1 |
| 898,915 | 6/1962 | United Kingdom | 71/DIG. 1 |

*Primary Examiner*—Joseph Paul Brust
*Attorney, Agent, or Firm*—Arne I. Fors; Robert F. Delbridge; David W. Wong

[57] ABSTRACT

A resinous herbicidal composition is provided in the form of a roller. The herbicide may be applied in lawns and gardens without the danger of being spread by wind or washed away by rain or dew. The herbicidal composition comprises a selected chemical herbicide or a number of herbicides homogeneously dispersed in a synthetic wax carrier. The synthetic wax is hard to break down by natural process, thus enabling the herbicides to remain on the weeds to control their growth.

8 Claims, No Drawings

HERBICIDAL COMPOSITION FOR WEED CONTROL

This application is a continutaion-in-part application of application Ser. No. 548,947 filed Feb. 11, 1975 now abandoned, which is a divisional application of application No. 440,940 filed Feb. 8, 1974 now U.S. Pat. No. 3,925,927.

BACKGROUND OF THE INVENTION

This invention relates to the control of weed growth in lawns and gardens and, more particularly, to chemical control of weed growth.

Weed control by the application of chemicals in lawns and gardens has been widely used, and has been found to be the most effective and convenient method for controlling weeds. In such method, chemical compounds called herbicides such as 2,4-dichlorophenoxyacetic acid are deposited by spraying onto the weeds. The herbicides will cause the weeds to defoliate and eventually to die, yet the herbicides are not harmful to grass.

Chemical herbicides are commonly provided to the user in the form of concentrated aqueous solutions. The user must dilute the aqueous solution into a workable solution of a predetermined concentration, and the dilute solution is sprayed over the entire lawn or in selected areas where weeds are growing actively. However, the herbicidal solution thus prepared cannot be applied to the lawn in rainy weather since it will either be highly diluted by the rain or be washed away thereby. Heavy dew will also weaken the effectiveness of the herbicidal solution. Also, it cannot be used in windy conditions even when the wind is moderate, because the spray and fume of the herbicidal solution can be easily carried away by the wind. The spray and fume of the herbicides carried by the wind are harmful to human as well as to other ornamental plants located in the neighbourhood, thus this presents a large problem to the effective application of such herbicides.

In order to avoid breathing in the fume and vapour of the herbicide, the user may drag the applicator behind him so that the harmful fume and vapour are blown away from him. This common practice also enables the user to avoid walking over the treated area so that the herbicidal solution of the applied area cannot cause contamination to his clothing. However, in doing so the user would not have a clear view of the area being treated and the applicator is not under his full control.

Furthermore, the herbicidal solution must be prepared carefully according to the recommended concentration and applied to the lawn evenly in a correct quantity. An excess amount of herbicides used will cause the grass to wilt or brown; a condition which is referred to as "burning" of the grass, making the lawn very unsightly and resulting in unhealthy grass growth. Also, herbicides are poisonous, and it is thus hazardous for the user to handle the concentrated aqueous solution of the herbicides in preparing the solution for use.

Attempts have been made to alleviate the problems of using liquid herbicides by admixing the herbicides with a solid base to form a solid herbicidal composition which can be applied by rubbing it on the weed plants. It does not require the user to prepare the solution and it can be used in a windy condition without the danger of spreading the herbicides to neighbouring trees and ornamental plants in herbaceous borders. However, known solid herbicidal compositions suffer the main drawback that they have a low melting point and they are readily melted by the solar heat after application to weeds such that they would run off into the soil or be diluted or washed away by rain or dew as in using liquid herbicidal compositions. Moreover, known solid herbicidal compositions when melted by the solar heat release the herbicides at an excessive rate to a point causing damage to the grass in the treated areas. This is mainly due to the fact that natural waxes have been used as the base carrier which have a low melting point. Also such solid herbicidal compositions often become very soft and tacky in summertime and the herbicides can be exuded from the composition due to the ambient heat. The exuded herbicides are then lost by volatilization into vapour which is harmful and may also cause contamination to other material placed nearby.

In spite of the low melting point, known solid herbicidal compositions have a low adhesiveness and they must be rubbed with a considerable pressing force so as to apply a satisfactory amount of the compositions on weed plants, and they are not adherent to wet weed plants.

Moreover, natural waxes break down readily in exposure to solar heat and atmosphere. Thus, they remain in the weed plants for a relatively short period without permitting the herbicides to act effectively on the weed plants.

PURPOSE OF THE INVENTION

It is the principal object of the present invention to provide solid herbicidal compositions which have a high melting point and high adhesiveness.

It is an object of the present invention to provide solid herbicidal compositions which remain on the weed plants for a relatively long period to effectively control their growth.

It is another object of the present invention to provide solid herbicidal compositions which may be conveniently used in the form of a roller and which may be applied easily to weed plants by rolling contact.

It is yet another object of the present invention to provide solid herbicidal compositions which mark the area that has been treated for ready identification.

SUMMARY OF THE INVENTION

The solid herbicidal compositions according to the present invention can be formed on the surface of a cylindrical core. The solid herbicidal compositions comprise selected herbicide material homogeneously dispersed in a base carrier comprising synthetic wax or synthetic resin or a mixture of these synthetic materials. The term "synthetic materials" used herein refers to materials which are produced solely by synthesizing chemical ingredients and which contain no natural compounds. The synthetic wax or resin is plasticized by a synthetic plasticizer which also enhances the bonding between the molecules of the wax and the herbicide material.

The synthetic wax contains no natural wax, becomes molten when heated to a temperature over about 200° F., and is chosen from the group consisting of N,N'-ethylene bis-stearamide and synthetic microcrystalline wax. The synthetic resin contains no natural ingredient and turns into a molten state when heated to a temperature over about 200° F. The synthetic plasticizer is chosen from the group consisting of phthalates and sebacate esters.

The herbicidal compositions have an extremely high adhesiveness and they may be applied to the weeds by simply rolling the roller over them. Only a slight downward pressure needs to be applied to the roller during application. By rolling contact, the composition will adhere to the leaves of the weeds in the form of a resinous coating which has a high melting point such that it cannot be readily melted by the solar heat, and it cannot be washed away by rain or dew water. The synthetic wax base contains no natural wax and mineral or vegetable oil, thus it is very hard to break down through natural process; and the herbicide material remains on the weeds for over a relatively long period of time to be thoroughly absorbed thereby and to control their growth. The application of such herbicidal compositions is not affected by wind, rain or dew. The adhesiveness of the present solid herbicidal compositions is so high that they can be satisfactorily applied to wet weed plants. The applicator can be pushed in front of the user such that it is completely under the control of the user who would also have a clear view of the area being treated.

DESCRIPTION OF SPECIFIC EMBODIMENT

The herbicidal compositions of the present invention comprise mainly a selected chemical herbicide material homogeneously dispersed in a synthetic wax or synthetic resin base. The following examples show some specific embodiments of the herbicidal compositions. These examples are included for illustration purposes only and in no way are intended to limit the scope of the invention.

EXAMPLE 1

Synthetic wax — 75 to 89% by volume
Synthetic plasticizer — 5 to 10% by volume
2(-4-chloro-2-methylphenoxy) propionic acid — 2 to 5% by volume
2-methoxy-3,6-dichlorobenzoic acid — 2 to 5% by volume
2-methyl-4-chlorophenoxyacetic acid — 2 to 5% by volume
Colouring pigment — optional Synthetic waxes such as N,N'-ethylene bis-stearamide commercially sold under the trade name of Calford wax, or microcrystalline synthetic wax can be used in the above composition. These synthetic waxes contain no natural waxes and they have a high hardness and high melting point such that they will turn into a molten state only when they are heated to a temperature of over about 200° F. Due to these characteristics, these synthetic waxes are commonly used as anti-slip agents, hardening and grease-proofing agents or protective coatings.

Synthetic plasticizers such as phthalates (e.g. dibutyl phthalate) and sebacate esters may be used as the plasticizer for plasticizing the hard synthetic wax to provide a high adhesive property. PARAPLEX WP1 (a trade mark of Rohm and Haas Company) can be used, which is an alkyd type polymeric material consisting mainly of oil modified sebacic acid alkyds. It is particularly advantageous to use since it is also a non-volatile material which would further reduce the volatility of the herbicidal compositions. The synthetic plasticizer not only improves the adhesiveness of the synthetic wax but also enhances the affinity of the synthetic wax molecules in bonding with the herbicide material. Furthermore, it increases the strength of the synthetic wax by raising the flash point and melting of the wax such that the latter is harder to break down when exposed to the sun and atmosphere.

In preparation, the synthetic plasticizer is added into the molten synthetic wax to form a molten mixture and the herbicide material is then added into the molten mixture. The herbicide material will homogeneously disperse throughout the plasticized synthetic wax base. The mixture when cooled has a resinous form which possesses a high adhesiveness to weed plants by mere rolling contact or attrition.

A mixture of chemical herbicides is used in order that the composition can be generally used for controlling all common types of weeds in lawns and gardens. It can be understood that any one selected kind of herbicide may be used such that the roller is suitable for controlling a specific type of weed.

The herbicide 2(-4-chloro-2-methylphenoxy) propionic acid is sold commercially under the trade name of MCPP Mecroprop, and 2-methoxy-3,6-dichlorobenzoic acid is available under the trade name CMPP dicamba and 2-methyl-4-chlorophenoxyacetic acid is commercially known as MCPA. These herbicides are highly effective for treating ordinary weeds commonly found in lawns and gardens such as black medic, chickweed, cocklebur, dandelion, knotweed, prickly lettuce, lamb's quarters, mustards, pennycress, pig weed, plantain, purslane, ragweed, ribgrass, sowthistle, speedwill, mossy stone crop, bull thistle, Canada thistle, vetch, yarrow, annual nettle, buttercup, charlock, common orache, cleavers, dovesfoot, cranesbill, fat hen, fumitory, runch, wild radish, sheppard's purse, wild turnip etc.

EXAMPLE 2

Synthetic resin (WING-TACK - a trade mark of Goodyear Tire and Rubber Co.) — 40 to 70% by volume
Synthetic plasticizer — 10 to 20% by volume
Ethoxylated nonyl-phenol (REXOL 25J) — 5 to 10% by volume
2(-4-chloro-2-methylphenoxy)propionic acid — 5 to 10% by volume
2-methoxy-3,6-dichlorobenzoic acid — 5 to 10% by volume
2-methyl-4-chlorophenoxyacetic acid — 5 to 10% by volume
Colouring pigment — optional In this example, synthetic resin is used as the main ingredient of the carrier base instead of synthetic wax. Similar to synthetic waxes, synthetic resins used also contain no natural compounds and have a high melting point. WING-TACK (a trade mark of Goodyear Tire and Rubber Co.) resin may be used for this purpose. Such synthetic resins normally have a tacky characteristic which may be modified with an appropriate amount of ethoxylated nonyl phenol which is commercially called Rexol 25J.

EXAMPLE 3

Synthetic wax — 15 to 39% by volume
Synthetic resin — 50 to 60% by volume
Dibutyl phthalate — 5 to 10% by volume
2(-4-chloro-2-methylphenoxy)propionic acid — 2 to 5% by volume
2-methoxy-3,6-dichlorobenzoic acid — 2 to 5% by volume
2-methyl-4-chlorophenoxyacetic acid — 2 to 5% by volume Colour pigment — optional In the above composition, a mixture of synthetic wax, either microcrystalline synthetic wax or N,N'-ethylene bis-stearamide, and synthetic resin is used as the carrier base for the herbicides. The WING-TACK synthetic resin used in Example 2 may be used in this composition. The synthetic resin mixes readily with the synthetic wax to form a tacky composition having a high adhesiveness and the high melting point of the synthetic wax and synthetic resin.

A selected small amount (about 2 to 4% by volume) of ethoxylated nonyl phenol again may be added into the composition to obtain a regulated amount of tackiness in the composition.

A fast-fading fugitive colouring pigment may be added into the above herbicidal compositions so that when applied to the lawn, the compositions will form a coloured coating on the weed plants and grass in the area which has been treated. This will eliminate any accidental repeated treatment of the same area, which not only results in waste of material and labour but may also result in damage to the grass in the treated area due to the excessive amount of herbicides thus applied thereon. Also, a large area of lawn may be treated in sections at separate times since only the treated sections are marked by the colour of the colouring pigment. The colouring pigment is preferably the fugitive type which will break down by the exposure to sun and natural atmosphere and its colour will disappear eventually without leaving any permanent colouring in the lawn.

The herbicidal compositions of the present invention can be formed as a layer over the cylindrical surface of a cylindrical core. The core may be made of plastics, pressed cardboard, wood or other similar type of material. It may have either a central longitudinal through bore or two central bores formed at both ends in order that the roller thus formed may be rotatably mounted on a handle. A plurality of indentations may be formed on the surface of the core to enhance the attachment of the solid herbicidal compositions to the cylindrical surface. These indentations may be in the form of longitudinal grooves or random depressions.

To construct the roller according to the present invention, the cylindrical core is centrally located vertically in a cylindrical mould, and the molten mixture of the herbicidal composition is introduced into the mould. When cool, the herbicidal composition forms a resinous layer over the cylindrical surface of the core.

In use, the roller is rotatably mounted on a bracket in a handle similar to the handle for a paint roller with the longitudinal bore or end bores of the core rotatably engaged with a single axle or two spaced axles forming the bracket. The roller can be simply rolled over the weeds locally or over the lawn generally such that a coating of the herbicidal composition will be rubbed off and adhered to the weeds or area of the lawn treated. The adhesiveness of the herbicidal compositions is so high that it can be applied even to wet weed plants. The coating cannot be washed off by rain or dew water, and no spray or fume will drift from the applicator to the neighbouring areas. The coating has a high melting point such that it would not be readily melted by the solar heat, and it will remain on the weeds for a long period of time and the herbicides in the composition are slowly and fully absorbed by the weeds to control their growth. In a test carried out, the herbicidal composition remained on the leaves of the weed plants for up to seven days.

It can be appreciated that fertilizers and insecticides instead of or in addition to herbicides may be used in the compositions to make rollers for applying fertilizers and/or insecticides in lawns and gardens. Alternatively, grass inhibiting chemicals such as 2,2-dichloropropionic acid commercially known as Dalapon or 6,7-dihydrodipyrido[1,2-a:2',1'-c] pyrazinediium ion (9,10-dihydro-8a,10a-diazoniaphenanthrene-2A) commercially known as Diquat may be used instead of the herbicides in order to control undesirable grass growth in vegetable fields, sidewalk cracks, driveways, patios, or selected areas in a garden. In such circumstances, the roller may be used in close proximity of ornamental plants without the risk of affecting the ornamental plants during application.

The embodiments which have been described are intended only to be illustrative of th inventive features involved; various other embodiments and modifications may be made by those skilled in the art without departing from the spirit and scope of the invention.

What I claim as new and desire to protect by Letter Patent of the United States is:

1. A solid herbicidal composition useable for controlling plant growth comprising
   75 to 89% by volume of synthetic wax, said synthetic wax containing no natural wax and becoming molten when heated to a temperature over about 200° F., and being chosen from the group consisting of N,N'-ethylene bis-stearamide and synthetic microcrystalline wax,
   5 to 10% by volume of synthetic plasticizer, said synthetic plasticizer being chosen from the group consisting of phthalates and sebacate esters, and
   6 to 15% by volume of herbicide material, said herbicide material comprising
   2 to 5% by volume of 2(-4-chloro-2-methylphenoxy) propionic acid,
   2 to 5% by volume of 2-methoxy-3,6-dichlorobenzoic acid, and
   2 to 5% by volume of 2-methyl-4-chlorophenoxyacetic acid.

2. A solid herbicidal composition according to claim 1 including an optional amount of fugitive colour pigment.

3. A solid herbicidal composition according to claim 1 including a growth inhibiting material chosen from the group consisting of 2,2-dichloropropionic acid and 6,7-dihydrodipyrido [1,2-a:2',1'-c] pyrazinediium ion (9,10-dihydro-8a,10a-diazoniaphenanthrene-2A).

4. A solid herbicidal composition comprising
   15 to 39% by volume of synthetic wax,
   50 to 60% by volume of synthetic resin,
   5 to 10% by volume of dibutyl phthalate,
   2 to 5% by volume of 2(-4-chloro-2-methylphenoxy)-propionic acid,
   2 to 5% by volume of 2-methoxy-3,6-dichlorobenzoic acid,
   2 to 5% by volume of 2-methyl-4-chlorophenoxyacetic acid,
   wherein said synthetic wax contains no natural wax and becomes molten only when heated to a temperature over about 200° F., and is chosen from the group consisting of N,N'-ethylene bis-stearamide and synthetic microcrystalline wax, and wherein said synthetic resin contains no natural ingredient and becomes molten when heated to a temperature over about 200° F.

5. A solid herbicidal composition according to claim 4 admixed with 2 to 4% by volume of ethoxylated nonyl phenol to produce a solid compound of reduced tackiness.

6. A solid herbicidal composition according to claim 5 including an optional amount of fugitive colour pigment.

7. A solid herbicidal composition for controlling plant growth comprising 40 to 70% by volume of synthetic resin, said synthetic resin containing no natural ingredient and becoming molten when heated to a temperature over about 200° F., 10 to 20% by volume of synthetic plasticizer, said synthetic plasticizer being chosen from the group consisting of phthalates and sebacate esters, 5 to 10% by volume of ethoxylated nonyl phenol, and 15 to 30% by volume of herbicide material, said herbicide material comprising 2 to 5% by volume of 2(-4-chloro-2-methylphenoxy)-propionic acid, 2 to 5% by volume of 2-methoxy-3,6-dichlorobenzoic acid, and 2 to 5% by volume of 2-methyl-4-chlorophenoxyacetic acid.

8. A solid herbicidal composition according to claim 7 including an optional amount of fugitive colour pigment added into the compound.

* * * * *